(12) United States Patent
Noonan et al.

(10) Patent No.: US 10,687,909 B2
(45) Date of Patent: Jun. 23, 2020

(54) ROBOTIC CONTROL OF IMAGING DEVICES WITH OPTICAL SHAPE SENSING

(71) Applicant: KONINKLIJKE PHILIPS N.V., Eindhoven (NL)

(72) Inventors: David Paul Noonan, New York, NY (US); Molly Lara Flexman, Melrose, MA (US); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 972 days.

(21) Appl. No.: 15/109,672

(22) PCT Filed: Dec. 11, 2014

(86) PCT No.: PCT/IB2014/066812
§ 371 (c)(1),
(2) Date: Jul. 5, 2016

(87) PCT Pub. No.: WO2015/110882
PCT Pub. Date: Jul. 30, 2015

(65) Prior Publication Data
US 2016/0324585 A1 Nov. 10, 2016

Related U.S. Application Data

(60) Provisional application No. 61/930,977, filed on Jan. 24, 2014.

(51) Int. Cl.
*A61B 34/32* (2016.01)
*A61B 34/30* (2016.01)
(Continued)

(52) U.S. Cl.
CPC ............... *A61B 34/32* (2016.02); *A61B 8/12* (2013.01); *A61B 34/20* (2016.02); *A61B 34/30* (2016.02);
(Continued)

(58) Field of Classification Search
CPC ......... A61B 34/32; A61B 34/30; A61B 34/20; A61B 34/25; A61B 34/35; A61B 34/37;
(Continued)

(56) References Cited

U.S. PATENT DOCUMENTS

| | | | |
|---|---|---|---|
| 6,425,865 B1* | 7/2002 | Salcudean | A61B 8/0875 600/111 |
| 7,930,065 B2* | 4/2011 | Larkin | B25J 19/025 700/245 |

(Continued)

FOREIGN PATENT DOCUMENTS

JP 2007007041 A 1/2007

*Primary Examiner* — Carolyn A Pehlke

(57) ABSTRACT

A system for tracking a device image includes an intraoperative imaging system (110) having a probe (146) configured to generate an image for a region. A shape sensing enabled instrument (102) is configured to have a portion of the shape sensing enabled instrument positionable relative to the region. The shape sensing enabled instrument has a coordinate system registered with a coordinate system of the intraoperative imaging system. A robot is configured to coordinate movement between the probe and the shape sensing enabled instrument such that movement of the shape sensing enabled instrument relative to the region causes the probe to be moved to maintain the shape sensing enabled instrument within the image.

14 Claims, 4 Drawing Sheets

(51) Int. Cl.
   *A61B 34/20*      (2016.01)
   *A61B 90/00*      (2016.01)
   *A61B 8/12*       (2006.01)

(52) U.S. Cl.
   CPC ...... *A61B 90/37* (2016.02); *A61B 2034/2061* (2016.02); *A61B 2034/301* (2016.02); *A61B 2090/378* (2016.02); *A61B 2090/3784* (2016.02)

(58) Field of Classification Search
   CPC .... A61B 2034/2046; A61B 2034/2059; A61B 2034/2061; A61B 2034/2063; A61B 2034/301; A61B 8/12; A61B 8/42; A61B 8/4209; A61B 8/4245; A61B 8/4254; A61B 8/4263; A61B 8/46; A61B 90/37; A61B 2090/378
   See application file for complete search history.

(56) References Cited

U.S. PATENT DOCUMENTS

| | | |
|---|---|---|
| 8,388,605 B2 | 3/2013 | Umemoto et al. |
| 9,430,717 B2 | 8/2016 | Denissen |
| 9,625,516 B2 | 4/2017 | Hopf et al. |
| 2002/0128552 A1* | 9/2002 | Nowlin .................. A61B 34/70 600/427 |
| 2007/0106147 A1 | 5/2007 | Altmann et al. |
| 2010/0274087 A1 | 10/2010 | Diolaiti et al. |
| 2013/0216025 A1 | 8/2013 | Chan et al. |
| 2013/0317356 A1 | 11/2013 | Ramachandran et al. |
| 2013/0324833 A1 | 12/2013 | Barley et al. |
| 2014/0257329 A1* | 9/2014 | Jang ....................... A61B 34/30 606/130 |

\* cited by examiner

ROBOTIC CONTROL OF IMAGING DEVICES WITH OPTICAL SHAPE SENSING

CROSS-REFERENCE TO PRIOR APPLICATIONS

This application is the U.S. National Phase application under 35 U.S.C. § 371 of International Application Serial No. PCT/IB2014/066812, filed on Dec. 11, 2014, which claims the benefit of U.S. Application Ser. No. 61/930,977, filed on Jan. 24, 2014. These applications are hereby incorporated by reference herein.

BACKGROUND

Technical Field

This disclosure relates to medical instruments and more particularly to robot control systems and methods using optical shape sensing technology.

Description of the Related Art

Robotic control of real-time imaging devices (such as ultrasound imaging or any kind of optical imaging) aims to simplify positioning of an imaging device during surgical and interventional procedures. The operator is permitted to perform either remote control or image-based control of the device.

A disadvantage of remote control using traditional input devices (e.g., joystick) is that mapping of a robot coordinate frame and frames of the imaging device with an output image is not explicitly known to the operator. This mapping is usually learned during the procedure and can result in prolonged operating times.

Image guidance has other issues. These issues may include that image guidance can track only targets that are within the visual field of the imaging device while the most challenging targets, those that are not in the field, continue to be inaccessible. Image guidance also requires targets to be tracked using image processing methods that can fail due to an obstructed field of view or poor quality of the image. For example, in ultrasound imaging, devices like catheters are difficult to track due to poor visualization of the catheter tip and low signal to noise ratio in ultrasound images. Furthermore, in 2D ultrasound, the devices can move outside of a viewing plane. In optical imaging, for example, with an endoscope, the field of view can be significantly smaller than an anatomical area of interest. Furthermore, in laparoscopic surgery, devices can leave the visual field, which can cause injury to tissue as the operator needs to use visual feedback of the operating site.

SUMMARY

In accordance with the present principles, a system for tracking a device image includes an intraoperative imaging system having a probe configured to generate an image for a region. A shape sensing enabled instrument is configured to have a portion of the shape sensing enabled instrument positionable relative to the region. The shape sensing enabled instrument has a coordinate system registered with a coordinate system of the intraoperative imaging system. A robot is configured to coordinate movement between the probe and the shape sensing enabled instrument such that movement of the shape sensing enabled instrument relative to the region causes the probe to be moved to maintain the shape sensing enabled instrument within the image.

Another system for tracking a device image includes an ultrasonic imaging system having a probe configured to generate an image for a region. A shape sensing enabled instrument is configured to have at least a portion of the shape sensing enabled instrument positionable relative to the region. A robot is configured to coordinate movement between the probe and the shape sensing enabled instrument. A robot control system includes a nested control loop including a first feedback loop that employs shape sensing feedback from the shape sensing enabled instrument and a second feedback loop that employs robot encoder information as motion feedback for the probe wherein the control system maintains a spatial relationship between the shape sensing enabled instrument and the probe such that movement of the shape sensing enabled instrument relative to the region causes the probe to be moved to maintain the shape sensing enabled instrument within the image.

A method for tracking a device image includes positioning a shape sensing enabled instrument within an internal region to be imaged; imaging the internal region of a subject with a probe for an intraoperative imaging system to generate an image for the region; registering a coordinate system of the shape sensing enabled instrument with a coordinate system of the intraoperative imaging system; robotically positioning the probe relative to the shape sensing enabled instrument such that the shape sensing enabled instrument is positioned within the image; and robotically repositioning the probe in accordance with movement of the shape sensing enabled instrument.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
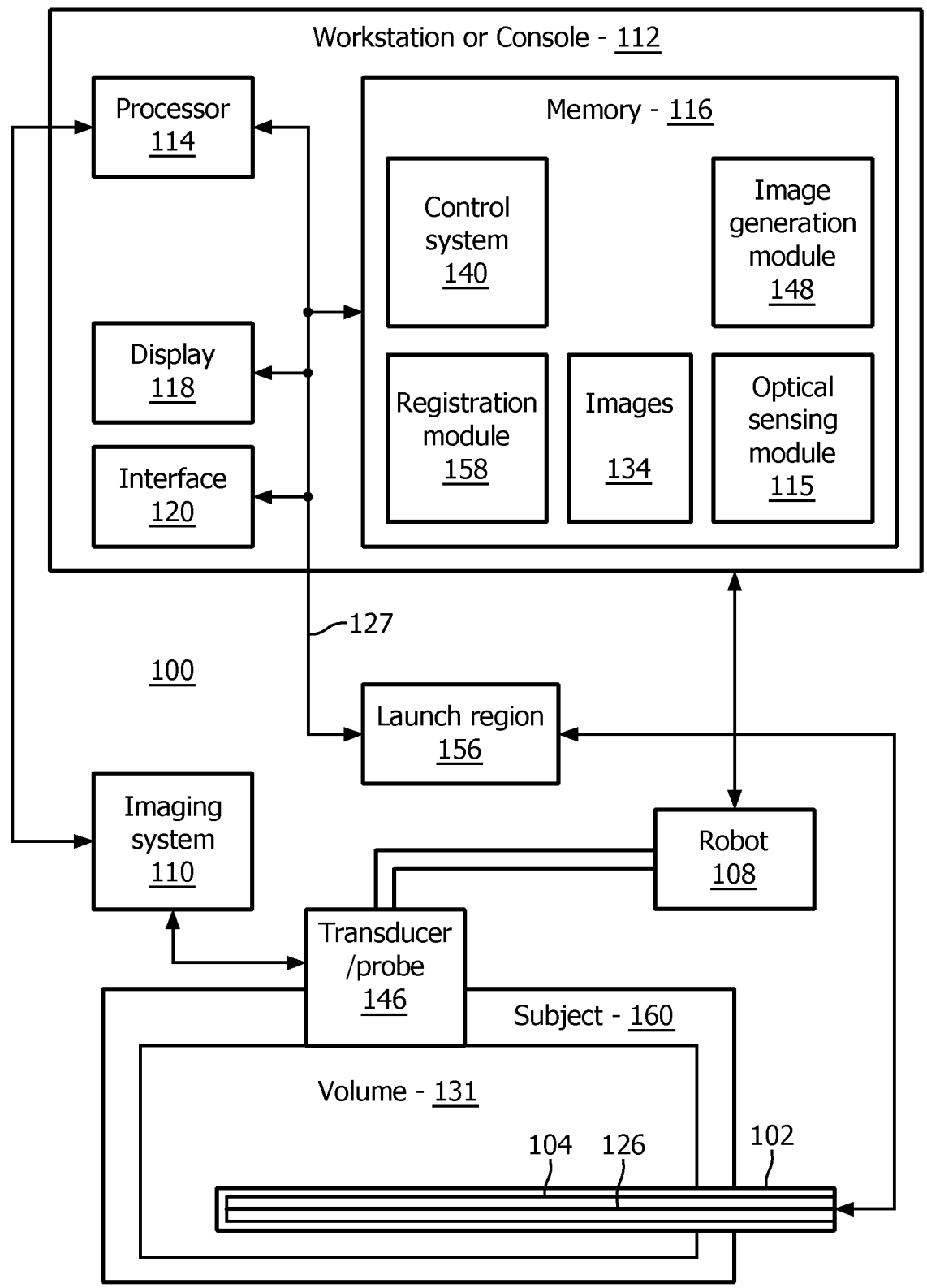
FIG. 1 is a block/flow diagram showing a system for image tracking configured to track a shape sensing enabled device or instrument with an imaging device using a robot in accordance with one embodiment.

In accordance with the present principles, systems, devices and methods are described, which provide control of a robot using optical shape sensing technology. Image guidance of a robotically controlled imaging device solves the afore-mentioned mapping problem by permitting an operator to choose targets from the most intuitive frame—an image frame. In accordance with the present principles, robotic control of an ultrasound probe is provided to intelligently track an optical shape sensing (OSS) enabled catheter or other device. A system and method are provided to visualize devices during medical procedures by sensing shape of the devices, registering that shape to a robot coordinate frame, and guiding the robot to bring those devices into a visual field of an imaging device. The present principles permit the repositioning of the imaging device to reach the targets that are not visible in a current view.

An optical shape-sensed interventional device may be employed to close a feedback control loop of a robotically actuated imaging probe. The robot uses a known position of the shape-sensed device with respect to an ultrasound volume to track the shape-sensed device and maintain the device within a field of view during a procedure. The intelligent tracking can also automatically select an optimal slice or plane to show the shape-sensed device in the image. Further, the tracking can consider how to optimize the image resolution of a selected plane. Potential ultrasound image sources may include a transesophageal echocardiogram (TEE) probe, a pediatric TEE, a micro TEE, a surface imaging probe (for example, a C5-2) or optical imaging probes (endoscopes, bronchoscopes, etc.). Other devices and procedures may also benefit from the present principles.

In one embodiment, optical shape sensing is employed to create a virtual ultrasound image. This may be done using a known transformation between, e.g., an ultrasound probe and a catheter or shape sensing enabled device to reformat the ultrasound image so that the image appears as though a transducer aperture were on the catheter or device. The optical shape-sensing catheter then can allow the aperture to be translated and rotated about the catheter or relative to the catheter so long as the virtual aperture remains within the ultrasound dataset. Also, based on the position of the catheter in the ultrasound volume, the ultrasound transmit sequence can be adapted to optimize the virtual ultrasound image. To keep the catheter within the ultrasound imaging volume or at a position relative to the ultrasound imaging volume, the ultrasound imaging probe can be controlled robotically using a known position from the shape sensing catheter. The robotic control can improve generation of the virtual images by aligning the imaging volume to the device and allowing repositioning of the probe for the generation of a virtual volume.

Potential ultrasound image sources may include internal ultrasound probes, such as, TEE; transrectal ultrasound (TRUS); single surface probes (e.g., linear, curved, sector, matrix); multiple surface probes (simultaneously or in sequence or both); etc. Potential registration between the ultrasound probe (e.g., head position) and the shape-sensing enabled device (e.g., catheter) may include shape-based sensing of the ultrasound probe (shape-to-shape registration prior to deployment); image-based registration of the ultrasonic probe (e.g., TEE probe head) using, e.g., EchoNav™, a model-based approach, x-ray based registration of the shape-sensed device, etc.; alternative tracking of the probe using technologies, such as, e.g., electromagnetic tracking of the TEE probe head (EM-to-shape registration prior to deployment), optical tracking of the hand-held probe, ultrasound-image based identification, etc.

The known position and plane of the device can be used to change the ultrasound transmit profile (through robotic mechanical positioning). Alternately, the ultrasound image could be used as input to drive the device towards the direction that is being visualized/targeted (for example, for intravascular ultrasound (IVUS) pullback). The present principles permit any shape sensing enabled device to be transformed into an intracardiac echocardiography (ICE) or IVUS device with the addition of an external ultrasound probe. Any device already enabled for optical shape sensing for navigational purposes can be repurposed to perform virtual IVUS with the addition of a standard ultrasound imaging probe.

The present principles apply to robotic control of an external or internal probe (e.g., ultrasound) for moving an ultrasound volume relative to a position of an optical shape sensing device, which may be employed to define an aperture for the volume. The optical shape sensing device may include a guide wire or catheter, but could be extended to endoscopes, bronchoscopes, and other such devices or applications.

It should be understood that the present invention will be described in terms of medical instruments; however, the teachings of the present invention are much broader and are applicable to any robotically controlled instruments using OSS enabled devices. In some embodiments, the present principles are employed in tracking or analyzing complex biological or mechanical systems. In particular, the present principles are applicable to internal tracking procedures of biological systems and/or for procedures in all areas of the body such as the lungs, gastro-intestinal tract, excretory organs, blood vessels, heart, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes, which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Referring now to the drawings in which like numerals represent the same or similar elements and initially to FIG. 1, a system 100 for robot control using a shape sensing enabled device or devices is illustratively shown in accordance with an illustrative embodiment. System 100 may include a workstation or console 112 from which a procedure is supervised and/or managed. Workstation 112 preferably includes one or more processors 114 and memory 116 for storing programs and applications. Memory 116 may store an optical sensing module 115 configured to interpret optical feedback signals from a shape sensing device or system 104. Optical sensing module 115 is configured to use the optical signal feedback (and any other feedback, e.g., electromagnetic (EM) tracking, ultrasound, etc.) to reconstruct deformations, deflections and other changes associated with a medical device or instrument 102 (also referred to as a shape sensing enabled device or instrument, an optical shape sensing (OSS) device, OSS catheter, catheter, etc.). In some embodiments, the medical instrument 102 may include a catheter, a guidewire, a probe, an endoscope, a robot, an electrode, a filter device, a balloon device, or other medical component, etc.

The shape sensing system or device 104 on instrument 102 includes one or more optical fibers (or fiber cores or channels) 126, which are coupled to the instrument 102 in a set pattern or patterns. The optical fibers 126 connect to the workstation 112 through cabling 127. The cabling 127 may include fiber optics, electrical connections, other instrumentation, etc., as needed.

Shape sensing system 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors (as discrete or continuous elements along the fiber). In an FBG sensor, the measurand (e.g., strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

Optical shape sensing (OSS) uses light along a multicore optical fiber for device localization and navigation during surgical intervention. The principle involved makes use of distributed strain measurement in the optical fiber using characteristic Rayleigh backscatter or controlled grating patterns. The shape along the optical fiber begins at a specific point along the sensor, known as a launch region 156 or z=0, and the subsequent shape position and orientation are relative to that point. Optical shape sensing fibers integrated into medical devices, such as catheters and guidewires, provide live guidance of the devices during minimally invasive procedures and can provide the position and orientation of the entire instrument 102.

In one embodiment, workstation 112 includes an image generation module 148 configured to receive feedback from the shape sensing device 104 (position data) as to where the sensing device 104 is or has been in a subject 160. An image volume (or data set) 131 is imaged within the subject 160 using an imaging system 110, such as an ultrasound imaging system, although other intraoperative imaging systems may be employed. An image or images 134 of a data set is/are collected from the imaging system 110 using one or more internal or external probes or transducers 146 (also referred to as a probe, probe head, ultrasonic probe head, TEE probe head, etc.) to map out the image volume 131. The images 134 can be displayed on a display device 118. The images 134 may be overlaid on, fused with or otherwise depicted along with other pre-operative or intra-operative images.

Workstation 112 includes the display 118 for viewing internal images of a subject (patient or other object) 160 or volume 131. Display 118 may also permit a user to interact with the workstation 112 and its components and functions or any other element within the system 100. This is further facilitated by an interface 120, which may include a keyboard, mouse, a joystick, a haptic device, or any other peripheral or control modality to permit user feedback from and interaction with the workstation 112.

In accordance with the present principles, the shape sensing enabled instrument 102 and an ultrasound probe or transducer 146 may have their movements coordinated using a robot system 108. The ultrasound probe 146 may be coupled to an ultrasound imaging system 110, which may be part of the console 112 or may be a separate unit. The ultrasound image 131 can be generated from a single transducer, e.g., a transesophageal echocardiogram (TEE) transducer, nasal TEE probe, or an external surface probe (such as, a C5-2 probe, etc.) and may include a volume (3D images), plane or slice (2D images). The ultrasound probe 146 may be an external probe or an internal probe. Although ultrasound imaging is described herein, other imaging modes may also be employed.

In particularly useful embodiments, the OSS enabled instrument 102 is maneuvered within the subject 160 to perform a function during a surgical procedure. As the OSS enabled instrument 102 is positioned within the subject, the robot system 108 tracks a portion of the instrument 102 (or instruments). A distinctive shape or feature on a distal end portion (or other portion) of the instrument 102 may be employed as a target for the imaging probe 146. The OSS enabled instrument 102 and the imaging probe 146 may be registered so that movement of the OSS enabled instrument 102 causes the robot system 108 to move the probe 146 accordingly. The probe 146 is moved along a surface of the subject 160 and needs to monitor pressure against the subject as well as acoustic coupling to ensure no harm to the subject 160 and proper imaging. The robot system 108 may be controlled using a control system 140. The control system 140 may also permit manual user controls and/or image based guidance. The control system 140 may include hardware, software or combinations thereof.

Registration between the probe 146 and the OSS enabled instrument 102 may be achieved in a plurality of ways. A registration module 158 may be included to handle registration operations for the system. One method of registration may include having the robot system 108 control motion for both devices. Other methods include registering coordinate frames of the probe 146 and the OSS enabled instrument 102 to a common coordinate frame, etc. Registration between the probe 146 and the OSS enabled instrument 102 may be established using other registration methods as well. For example, such registration techniques to register the ultrasound probe 146 (head position) and the OSS enabled instrument 102 (e.g., shape-sensed catheter) may include employing EchoNav™ registration of the probe head (x-ray based registration of the shape-sensed device); electromagnetic tracking of the probe head (EM-to-shape registration prior to deployment), optical shape sensing tracking of the probe head (shape-to-shape registration prior to deployment), etc.

In another embodiment, a fluoroscopy-based registration may be performed. For example, a TEE probe head 146 can be registered to an x-ray image (e.g., as in EchoNav™) and the OSS catheter 102 can be registered to the x-ray image as well, providing a transformation between the TEE probe head 146 and the OSS enabled instrument 102. The TEE probe head 146 would need to be tracked dynamically (e.g., by robot system 108) via x-ray whereas the OSS enabled instrument 102 only needs to be registered to the x-ray image once. In yet another embodiment, an alternatively tracked transducer 146 and a shape-sensed catheter 102 may be employed. A transducer or probe head 146 can be tracked using other tracking technologies (e.g., electromagnetic tracking or optical tracking for an external transducer) and the launch fixture 156 of the optical shape sensing enabled instrument 102 can be registered to that alternate tracking solution. Other registration techniques and methods are also possible and are contemplated in accordance with the present principles.

In one embodiment, to allow an appropriate generation of a view in a correct plane of a catheter or instrument 102, a control scheme of the robot control system 140 can be modified so that the US probe 146 is guided by a shape of the proximal end of the catheter 102. In this embodiment, the shape of the catheter 102 is fit to a plane. The orientation of the plane to the points in the probe workspace is optimized so that the instrument 102 in a physical image plane is maximized. In a further embodiment, the robot 108 can move to an optimal position to generate an ultrasound volume and then go back to an original position to visualize some other features (e.g., another device or anatomical feature). The position of such features can be 'tagged' in the ultrasound volume (and thus probe coordinate system) by saving the position of the distal tip (or other position) of the instrument 102 at a discrete moment in time. The location can then be re-imaged by the probe 146 even when the shape sensed instrument 102 has been navigated away from the location.

The optimal plane may be determined through the distal portion of the instrument 102 to determine the optimal position of the probe 146. Since this motion will be known from robot encoders and robot workspace, the spatial relationship is known and can be visualized in the reference frame. Those parts of the volume that are visible in the new probe position can be updated from the physical volume and may be shown in the context of the "off-line" volume visualization. The robot system 108 can be moved between two different positions to update the entire volume, loop between images, etc.

In three-dimensional imaging, the ultrasound volume 131 may be resampled to extract only a slice (or subset of the volume 131) that includes the instrument 102. Specifically, this could be performed by extracting a plane that best shows the distal portion of the instrument 102. In two-dimensional imaging, when moving the robot system 108, the 2D slice could be adjusted to best capture the plane of the instrument 102. Extracting the images of the instruments 102 may be performed by employing pattern recognition or other image processing technique (e.g., using image processor 148) to identify the instrument 102 in the image. The instrument 102 position may also be determined using the registration information, and an optimal slice or position may be determined based on user preference. Other methods may also be employed and are contemplated.

In one embodiment, to allow an appropriate generation of a view in a correct plane of a catheter 102, a control scheme can be modified so that the US probe 146 is guided by a shape of the proximal end of a catheter 102. In this embodiment, the shape of the catheter 102 is fit to a plane. The orientation of the plane to the points in the probe workspace are optimized so that the plane is aligned to a desired view of the instrument 102, e.g., an angle between a plane of the shape of the instrument 102 and a physical image plane may be minimized. In a further embodiment, the robot system 108 can move to an optimal position to generate an ultrasound volume and then go back to the original position to visualize some other features (e.g., another device or anatomical feature). The optimal plane may be determined through the distal portion of the instrument 102 to determine the optimal position of the probe head 146. Since this motion will be known from robot encoders and robot workspace, the spatial relationship is known and can be visualized in the reference frame. Those parts of the volume that are visible in the new probe position can be updated from the physical volume and shown in context of the "off-line" volume visualization. The robot system 108 can be moved between two different positions to update the targets or the entire volume.

Figure 2:
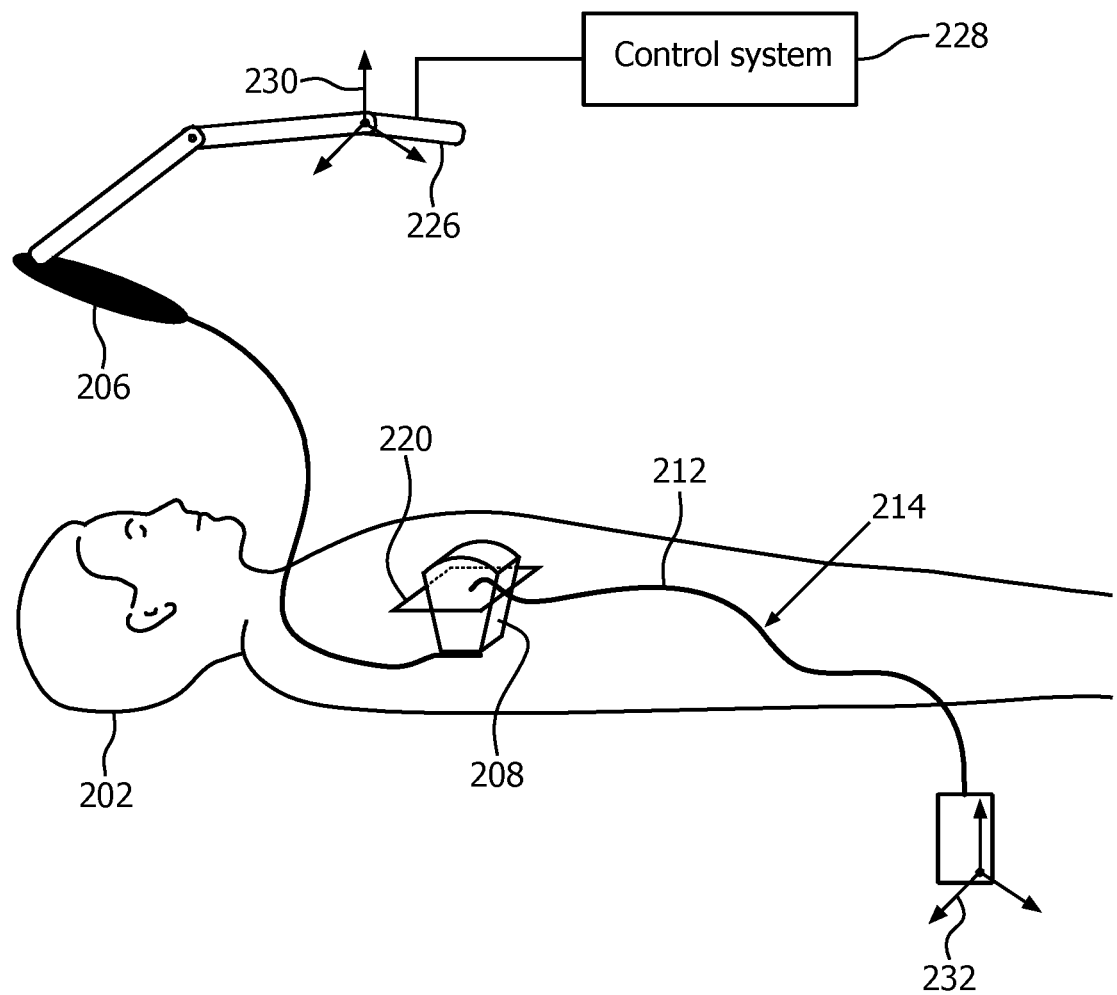
FIG. 2 is a cross-sectional view of a subject showing an internally disposed transducer following a shape sensing enabled device or instrument for imaging a volume or plane in accordance with one embodiment.

Referring to FIG. 2, a cross-sectional diagram shows a patient 202 having a TEE transducer 204 on a TEE probe 206. The transducer 204 is passed through the esophagus of the patient 202 and creates an ultrasonic imaging volume 208 within the patient 202. The imaging volume 208 overlaps a region or regions in which a shape sensing enabled instrument 214 (e.g., a catheter) has an optical shape sensing fiber(s) 212 therein. The instrument 214 may be provided through a port or through a natural orifice in the patient. The imaging volume 208 is positioned at a selected location and orientation based on the instrument 214. The TEE probe 206 is robotically controlled and used to visualize the shape sensing enabled instrument 214, which is depicted as an intravascular catheter. An optimal plane 220 of the three dimensional imaging volume 208 is selected based upon a distal shape of the catheter 214. The distal shape of the catheter 214 is employed as a mechanism for defining the viewing plane 220, which in particularly useful embodiments, includes the visualization of the tool within the viewing plane 220. That is, the intravascular shape-sensed catheter 214 is visualized using the robotically controlled TEE probe 206 with the optimal slice or plane 220 configured for display within the 3D imaging volume 208 in accordance with a shape of the distal portion of the instrument 214. Examples of pre-curved intravascular catheter shapes, which could be identified to define the viewing plane may include, e.g., the shapes of instruments provided by, e.g., Cobra™, Berenstein™, SIM2™, etc. Customized shapes may also be employed.

During a clinical procedure, the operator may need to maintain the instrument 214 to be within the ultrasound field of view (FOV). During interventional procedures, the instrument 214 may be moving constantly or intermittently as the operator navigates between relevant clinical targets. An example of switching between a plurality of locations may include when an interventional cardiologist navigates a catheter towards a mitral valve of the heart to deploy a device such as a clip or the like. There may be periodic motion due to heartbeat or breathing that moves the instrument 214 in and out of the imaging plane. In some clinical applications, multiple targets may need to be visualized during a procedure. For example, in the case of a paravalvular leak, the interventionalist would like to toggle the view between the leak itself and a number of catheters that may be employed to close the leak. As the field of view may be limited, the ultrasonic volume may not be able to visualize regions all at once.

In accordance with present principles, the shape sensing system 212 is configured to interrogate shape in a plurality of positions or regions. There may be multiple shape sensing systems 212 employed on or with one or more tools or instruments used during the procedure. These tools or instruments may include catheters or any other devices. The shape sensing system(s) 212 preferably includes one or more optical fibers embedded therein. The probe 206, e.g., an ultrasonic probe, such as a TEE probe, is configured to acquire 2D or 3D images. A robotic system 226 is configured to move the probe according to commands from a robot control and/or user interaction system 228.

In one embodiment, a TEE probe 206 is inserted into the patient 202 to visualize the heart. Shape sensing enabled instruments (catheters) 214 are introduced into the heart to perform the procedure. The user selects multiple targets (catheters or other devices with shape sensing fibers integrated therein) to have their coordinate system(s) 232 registered to a robot coordinate frame 230 and subsequently brought into a visual field of the ultrasound probe 206.

During the procedure, the user can select different modes of robot control. These may include a continuous mode selected by the user so that the robot continuously tracks a device 214 keeping the device 214 in the field of view. Another mode includes a static mode where the user can select this mode so that the robot moves to an explicit command to visualize a specific target without continuous updating of the position. Another mode can include a toggle mode where the user can select this mode so that the robot visualizes all targets in a loop (e.g., sequentially displaying each view). This mode can be useful to verify position and status of all devices and anatomical structures. Other modes are also contemplated which may include the described modes or other modes. For example, a split screen mode may be employed instead of the toggle mode to view a plurality of targets concurrently.

Figure 3:
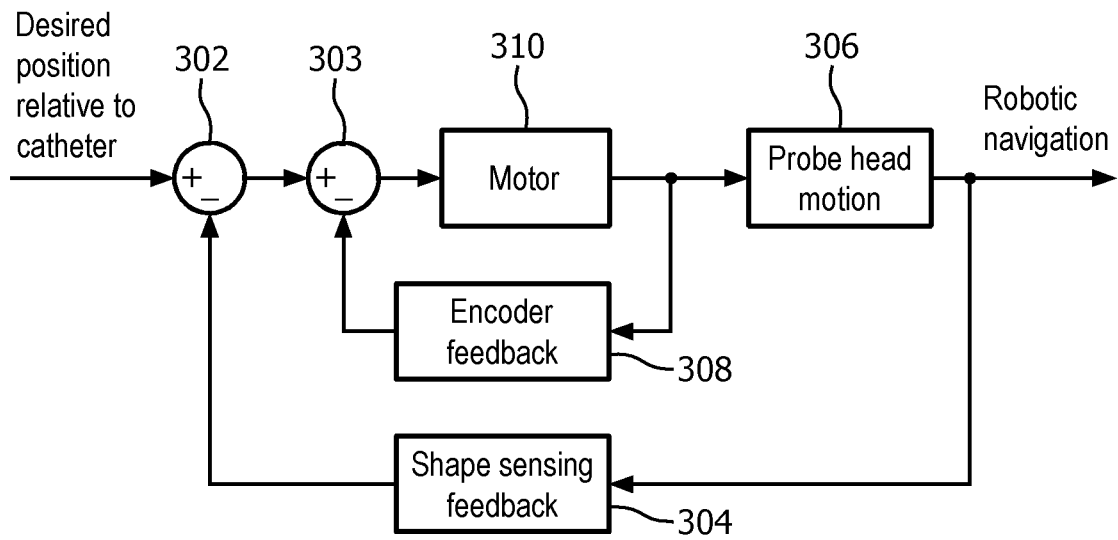
FIG. 3 is a schematic diagram showing a nested control loop for a robot control system in accordance with one embodiment.

Referring to FIG. 3, a nested closed loop feedback control system 300 is shown in accordance with one illustrative embodiment. The control system 300 may be employed to control the robot (108, FIG. 1, 226, FIG. 2). In this control system 300, a higher-level control loop 302 uses a known position of a catheter distal tip (shape sensing feedback 304) with respect to an ultrasound probe head 306 as input to a lower level controller 303. This lower level controller 303 monitors encoder position (encoder feedback) 308 and updates a motor position 310 accordingly. The control scheme of FIG. 3 can be employed for any type of robot and imaging device. The illustrative nested control loop 300 utilizes the shape sensing feedback 304 to robotically control the ultrasound volume (probe head 306) to maintain a fixed relationship with respect to the shape sensed interventional device (102, FIG. 1, 214, FIG. 2). The ultrasound probe position is adjusted by the robot to bring the catheter within the ultrasound field of view whether at some discrete time or in a continuous loop.

Referring again to FIG. 2, during the adjustment, the robotic control 228 needs to concurrently consider a plurality of factors as feedback data. For example, the motion of the probe head 206 needs to result in moving the imaging volume 208 or 2D slice 220 so that the device 214 is within the field of view. The robot control 228 needs to monitor contact force between the probe head 206 and tissue surface to ensure excessive force is not applied while maintaining sufficient force to ensure acoustic coupling. Other physical constraints of the ultrasound probe 206 may also need to be considered (for example, the TEE probe 206 may have a bounded range of possible positions). In the case of the robotically controlled TEE probe 206, the control of the robot 226 may include the control of two dials for changing position of a curved probe tip of the probe 206.

Figure 4A:
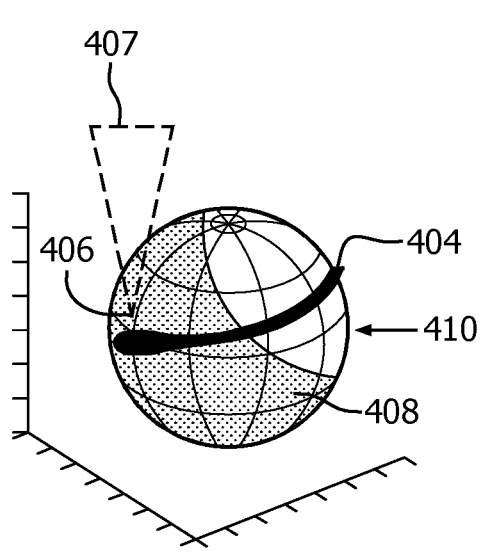
FIG. 4A is a diagram showing a starting image for showing a range of motion possible by a probe in accordance with the present principles.
Figure 4B:
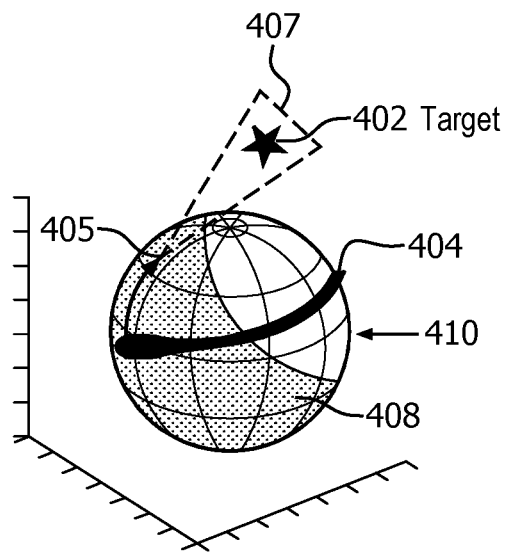
FIG. 4B is a diagram showing a target image for showing the range of motion possible by a probe in accordance with the present principles.

Referring to FIGS. 4A and 4B with continued reference to FIG. 2, an example of how the field of view of the TEE probe (206) can be adjusted to image a target 402 by steering a probe head 404 from a starting position 406 in FIG. 4A towards a target position 405 in FIG. 4B. A textured area 408 on a surface of a sphere 410 represents a permissible range of motion of the TEE probe (206) when controlled via dials. Every point on the sphere 410 has an inherent orientation 407 of the probe head 206, i.e., a corresponding image volume. The points of the sphere 410 and the volume orientations 407 associated with those are a characteristic of the probe 206 and can be stored in the robot control system 228 in a lookup table or other data storage structure. Once the target 402 is selected in the coordinate frame 230 of the robot 226, an ideal orientation of the US volume 208 is computed so that the target 402 is in the middle of the volume 208. This orientation is matched to a closest orientation in the lookup table, which is matched to the probe position.

The robot 226 attempts to reach the position by controlling, e.g., two dials while limiting force to the tissue. Pressure sensors or other sensors or measurements (motor current, for example) may be employed as feedback for satisfying there constraints. If no excessive force is applied in the motion, the robot 226 will reach the most optimal position to view the target 402. If the force limit is reached, the viewpoint of the imaging device will be suboptimal but will be the best possible viewpoint given the constraints.

Robotic control of imaging devices may have a multitude of implementations for control of ultrasound probes. For example, a system to control the dials on the handle of TEE probes and robotically control the position of the steerable probe tip may be employed, as well as other robot systems and methods.

To reduce the impact on the clinical workflow, the ultrasound probe(s) can be robotically controlled to maintain the catheter position within the ultrasound dataset. In the event that ultrasound quality degrades or is lost due to lack of coupling or pressure between the ultrasound transducer head and the surface (detected via image processing or manual observation), a robot can detect and compensate for this (by, e.g., increasing pressure or releasing gel to the surface) and then continuing to perform imaging. The robotic control can concurrently maintain the imaging volume, can optimize a physical position of the transducer for the image resolution, and can work within the physical constraints of the clinical application to maintain suitable contact with the tissue for imaging, while minimizing the forces on the patient. In the case of the robotically controlled TEE probe, the control of the robot may include control of two dials of the TEE probe for changing position of the curved probe tip.

The present principles apply to any robotic control of an imaging probe (e.g., ultrasound) using input from a shape-sensed instrument. This applies to guide wires, catheters (manual and robotic), etc., and can be extended to other devices and applications, e.g., endoscopes, bronchoscopes, and other such applications.

Figure 5:
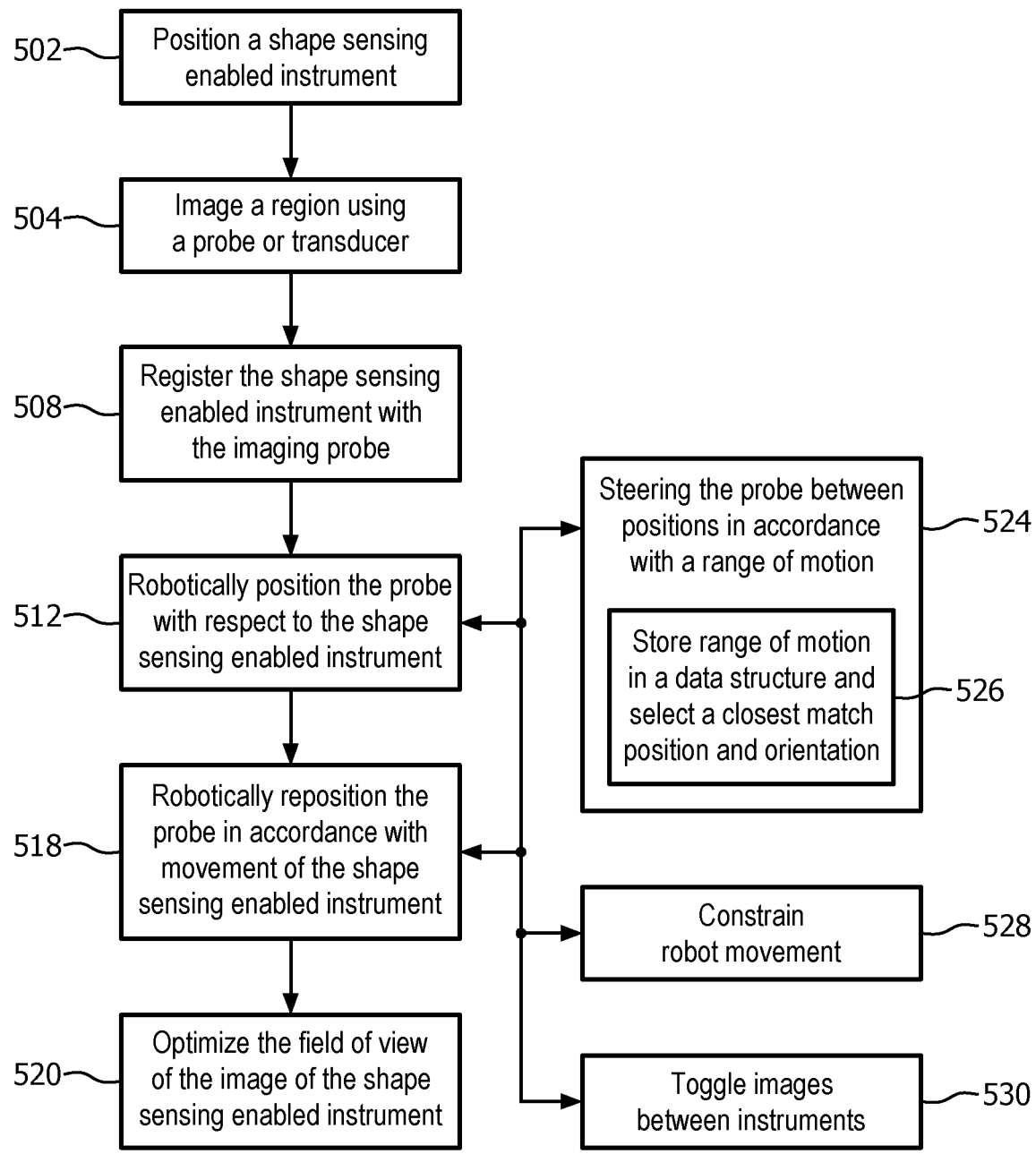
FIG. 5 is a flow diagram showing a method for physically tracking a shape sensing enabled device or instrument with an imaging probe using a robot in accordance with an illustrative embodiment.

Referring to FIG. 5, a method for physically tracking an image of a device is shown in accordance with illustrative embodiments. In block 502, a shape sensing enabled device or instrument is positioned within an internal region to be imaged. The shape sensing enabled device may include a catheter or other instrument. In block 504, the internal region of a subject is imaged using a probe and/or transducer of an intraoperative imaging system to generate an image for the region. The probe may include an ultrasound probe, although other imaging devices may be employed. The image may include a two-dimensional or a three-dimensional image.

In block 508, a coordinate system of the shape sensing enabled device is registered with a coordinate system of the intraoperative imaging system. This may be performed using a plurality of different methods. In block 512, the probe is robotically positioned relative to the shape sensing enabled device such that the shape sensing enabled device is positioned within the image. The robot may be programmed to center the shape sensing enabled device in the image, although other geometric arrangements or relationships may be employed.

In block 518, the probe is robotically repositioned in accordance with movement of the shape sensing enabled device. As the shape sensing enabled device moves, the probe tracks this movement to ensure that the shape sensing enabled device and/or the surrounding region of interest remains in the field of view being displayed. In block 520, the image from the intraoperative imaging system is optimized to provide a field of view that includes the shape sensing enabled device or other preferred view. The optimization may include maximizing a size of the device in the image, minimizing the size of the device in the image, centering the device in the image, etc.

In block 522, positioning or repositioning the probe may include steering the probe between a start position and a target position in accordance with a range of motion permitted between the start position and the target position. In block 524, the range of motion may be stored in a data structure, such as a lookup table. In block 526, the probe may be steered to a nearest position, stored in the lookup table that corresponds closest to the target position.

In block 528, robot movement is constrained to, e.g., provide acoustic or other coupling between the probe and a subject, prevent harm to a patient, limit motion of the robot, etc. In block 530, the robot may be controlled such that the robot moves the probe between a plurality of shape sensing enabled devices or instruments to toggle between images.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for robotic control of imaging devices with optical shape sensing (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for tracking and coordinating movement of a probe of an intraoperative imaging system with movement of a shape sensing enabled instrument, wherein a probe head on a curved end portion of the intraoperative imaging system is configured to generate an image of an image region of a subject;

the shape sensing enabled instrument having at least an end portion moveable in the subject relative to a target region, the shape sensing enabled instrument having a coordinate system, the shape sensing enabled instrument coordinate system being registered with a coordinate system of the intraoperative imaging system;

a robot configured to steer the probe head to move along points on a sphere between a start position and a target position, the points on the sphere defining a range of motion permitted between the start position and the target position, each of the points on the sphere corresponding to an orientation of the image region, the target position being a point on the sphere which orients the image region to include at least the end of the shape sensing enabled instrument;

a robot control system configured to receive an output from the shape sensing enabled instrument indicative of a location of the end portion of the shape sensing enabled instrument and recompute the target position as the end portion of the shape sensing enabled instrument moves to maintain the end portion of the shape sensing enabled instrument in the image region and control the robot to move the probe head to the recomputed target position.

2. The system as recited in claim 1, wherein the probe head includes an ultrasonic probe and the image includes a two-dimensional or a three-dimensional image.

3. The system as recited in claim 1, wherein the robot control system is configured to store the points on the sphere defining the range of motion in a lookup table, the robot control being configured to steer the probe head to one of the points on the sphere nearest the recomputed target position.

4. The system as recited in claim 2, wherein the probe head is configured to be positioned in a tubular body part and the robot control is configured to control the robot to press the probe head against the tubular body part with a pressure that acoustically couples the ultrasonic probe to the tubular body part without harming the tubular body part.

5. The system as recited in claim 1, wherein the robot control includes a nested control loop having a first feedback loop that feeds back shape sensing enabled instrument location from the shape sensing enabled instrument and a second feedback loop that feeds back probe motion feedback from a robot encoder to maintain the spatial relationship between the shape sensing enabled instrument and the probe wherein said first feedback loop is a higher level control loop than the second feedback loop.

6. The system as recited in claim 1, further comprising a plurality of shape sensing enabled instruments and the robot control is configured to toggle the probe head among points on the sphere to sequentially put the ends of each of the plurality of shape sensing enabled instruments in the image region.

7. The system as recited in claim 1, wherein a size of the sphere is determined by a geometry of the curved probe end portion and defines the permitted range of motion for the probe head, the robot control system being configured to store the permitted range of motion information in a lookup table, the robot control system being configured to steer the probe head to a point stored in the lookup table nearest to the target position.

8. A system for tracking of a probe and an instrument where an image is acquired by the probe, the system comprising:
a transesophageal echocardiogram (TEE) probe carrying an ultrasound imaging transducer configured to generate an ultrasound image of an image region in a cardiac region of a subject outside of an esophagus of the subject;
the instrument including a shape sensing enabled catheter configured to have at least an end portion of the catheter movably disposed in the cardiac region of the subject and to output a catheter signal indicative of a location and orientation of the end portion of the catheter;
a robot configured to steer the ultrasound imaging transducer and the image region, the robot including an encoder which outputs encoder information indicative of movement of the TEE probe, the ultrasonic imaging transducer, and the image region; and
a robot control system configured to control the robot to move the TEE probe along the esophagus to a location adjacent the heart and to steer the probe head along a sphere segment in a robot frame of reference representing a permissible range of motion of the probe head, each of a plurality of points on the spherical segment corresponding to a location and orientation of the image region, the robot control system including a nested control loop including a first feedback loop that feeds back the catheter signal and a second feedback look that feeds back the encoder information to control the TEE probe to maintain a spatial relationship between the end portion of the catheter and the TEE probe to maintain the catheter end portion within the image region.

9. The system as recited in claim 8, wherein the image includes a two-dimensional or a three-dimensional image.

10. The system as recited in claim 8, wherein the robot is configured to acoustically couple with the esophagus and includes a pressure sensor, the robot control system being configured to control the probe end portion to maintain acoustic coupling and prevent harm to a patient.

11. The system as recited in claim 8, further comprising a plurality of shape sensing enabled catheters, the catheters having probe end portions in different locations, some different locations being in different image regions corresponding to different points on the spherical segment, and wherein the robot control system is configured to toggle the TEE probe between imaging end portions of the plurality of shape sensing enabled catheters.

12. The system as recited in claim 8, further including:
a display device configured to display the ultrasound image.

13. A method for imaging an end portion of a surgical instrument configured for being inserted into and moved in an interior of a subject comprising:
positioning the end portion of the surgical instrument in an internal region to be treated and outputting an instrument signal indicative of a location and orientation of the end portion of the surgical instrument;
inserting a probe head carrying an ultrasound imaging transducer through a tubular structure internal to the subject to a location adjacent the region to be treated, the ultrasound imaging transducer being configured to image of an imaging region;
steering the probe head from a start position to a target position in accordance with a range of permitted motion between a start position and a target position, the range of permitted motion including a spherical section, each of a plurality of points on the spherical section corresponding to a location and an orientation of the imaging region, the target position corresponding to one of the points on the spherical section corresponding to a location and orientation of the imaging region that includes the end portion of the surgical instrument;
imaging the internal region to be treated of the subject with the ultrasound imaging transducer to generate an image for the region to be treated including the end portion of the surgical instrument;
registering a coordinate system of the surgical instrument with a coordinate system of the probe head;
as the end of the surgical instrument moves, repositioning the probe head along the spherical segment to maintain the surgical instrument end portion positioned within the imaging region.

14. The method as recited in claim 13, further comprising adjusting a field of view of the ultrasonic imaging transducer.

* * * * *